United States Patent [19]

Berlati et al.

[11] Patent Number: 5,656,277
[45] Date of Patent: Aug. 12, 1997

US005656277A

[54] NOR- AND HOMO- BILE ACIDS DERIVATIVES AS ABSORPTION ENHANCERS FOR MEDICAMENTS

[75] Inventors: Fabio Berlati; Giancarlo Ceschel; Aldo Roda; Enrico Roda; Celestino Ronchi, all of Pero, Italy

[73] Assignee: Monteresearch s.r.l., Pero, Italy

[21] Appl. No.: 360,833

[22] PCT Filed: Jun. 15, 1993

[86] PCT No.: PCT/EP93/01508

§ 371 Date: Dec. 28, 1994

§ 102(e) Date: Dec. 28, 1994

[87] PCT Pub. No.: WO94/00155

PCT Pub. Date: Jan. 6, 1994

[30] Foreign Application Priority Data

Jun. 30, 1992 [IT] Italy .................. MI92A1601

[51] Int. Cl.$^6$ .............. A61K 9/02; A61K 9/08; A61K 9/20; A61K 31/19
[52] U.S. Cl. .......... 424/400; 424/435; 424/451; 424/464; 424/436; 424/489; 514/169; 514/171; 514/182; 514/553; 514/569
[58] Field of Search ................ 424/435, 400, 424/456, 451, 464, 489; 514/169, 171, 182, 553, 569

[56] References Cited

FOREIGN PATENT DOCUMENTS 0128831  9/1984  European Pat. Off. .
0135782  4/1985  European Pat. Off. .

OTHER PUBLICATIONS

Nakada, J. Pharmacobio–Dyn, 11 (6), 395–401 1988.
Murakami, Chem. Pharm. Bull, 32 (5), pp. 1948–1955 1984.

*Primary Examiner*—Gollamudi S. Kishore
*Attorney, Agent, or Firm*—Griffin, Butler, Whisenhunt & Kurtossy

[57] ABSTRACT

The use of nor- and homo-bile acids derivatives as absorption enhancers for medicaments is described. Said derivatives show the advantage of improving the absorption of medicaments through mucosae without being metabolized by the intestinal flora, thus allowing a fast excretion. Moreover, the derivatives of the invention have a negligible toxicity.

15 Claims, No Drawings

NOR- AND HOMO- BILE ACIDS DERIVATIVES AS ABSORPTION ENHANCERS FOR MEDICAMENTS

The present invention relates to the use of nor- and homo-bile acids derivatives (hereinafter named NORAB and HOMOAB, respectively) as absorption enhancers for medicaments.

Particularly, the invention relates to the use of nor- and homo-bile acids derivatives having respectively the following formulae:

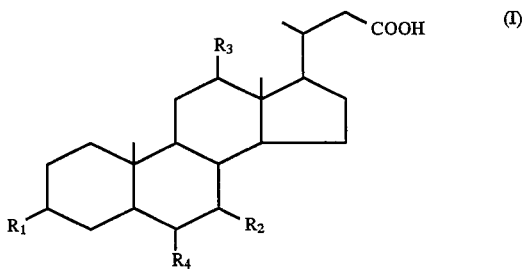

wherein:

|    | $R_1$  | $R_2$  | $R_3$  | $R_4$  |
|----|--------|--------|--------|--------|
| a) | α-OH   | α-OH   | H      | H      |
| b) | α-OH   | β-OH   | H      | H      |
| c) | α-OH   | H      | α-OH   | H      |
| d) | α-OH   | H      | β-OH   | H      |
| e) | α-OH   | H      | H      | β-OH   | corresponding to:

Ia) norchenodeoxycholic acid
Ib) norursodeoxycholic acid
Ic) nordeoxycholic acid
Id) 24-nor-[3α,12β-dihydroxy-5β-cholan-23-oic] acid
Ie) 24-nor-[3α,6β-dihydroxy-5β-cholan-23-oic] acid and

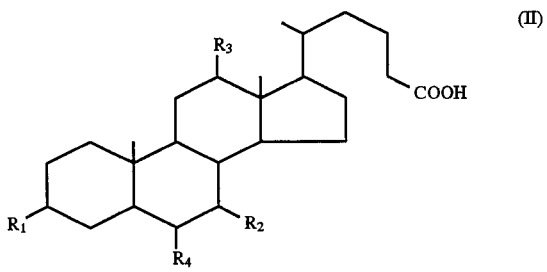

wherein:

|    | $R_1$  | $R_2$  | $R_3$  | $R_4$  |
|----|--------|--------|--------|--------|
| f) | α-OH   | α-OH   | H      | H      |
| g) | α-OH   | β-OH   | H      | H      |
| h) | α-OH   | H      | α-OH   | H      |
| i) | α-OH   | H      | β-OH   | H      |
| l) | α-OH   | H      | H      | β-OH   | corresponding to:

IIf) homochenodeoxycholic acid
IIg) homoursodeoxycholic acid
IIh) homodeoxycholic acid
IIi) 24-homo-[3α,12β-dihydroxy-5β-cholan-23-oic] acid
IIl) 24-homo[3α,6β-dihydroxy-5β-cholan-23-oic] acid.

It is also an object of the invention the use of the corresponding NORAB and HOMOAB conjugated respectively in $C_{23}$ and $C_{25}$ with taurine, glycine and alanine.

The present trend for pharmacological therapy, particularly in the case of slight disorders or of treatments involving multiple administrations repeated in time, and therapies for conscious patients, is the self-administration by the patient itself. From this point of view, the preferred administration routes are the enteral, i.e. buccal, rectal and intranasal ones.

The medicament administered through these routes, once released from the pharmaceutic form containing it (tablet, suppository, aerosol, and the like), must cross the different mucosae coating the gastrointestinal tract and the nasal cavity, in order to enter the circulatory stream and be distributed in the various body districts thus reaching the action site.

Due to the complex nature of the mucosae and the different chemical structure of the medicaments, the crossing of the mucosae involves different difficulties, depending on the kind of medicament and the type of mucosa.

One of the main problems involved in the design of medicaments consists in the need to give the pharmacologically active compound those hydrophilic characteristics which are generally required to have the active principle dissolved in the biological liquids (serum, interstitial liquid) and sometimes also lipophilic characteristics to cross the mucosa, which generally consists of a more or less complex cell barrier.

This approach finds a number of difficulties from the viewpoint of the medicament design, both in the synthesis and in the pharmacokinetic expectation.

A different approach to this problem consists in combining the active principle with a compound enhancing the absorption of the medicament through the mucosa.

Due to the single chemico-physical peculiarities of the different medicaments, up to now it was necessary to look for absorption enhancers suitable for both the considered medicament and the involved mucosa.

Bile acids (BA) are natural detergents capable of forming, with other poorly water-soluble medicaments, mixed micells with phospholipids and cholesterol at a relatively low concentration (1–4 mM).

Moreover, thanks to the structure thereof, they are also relatively lipophilic (log p=2÷4) and therefore they can passively cross the biologic membranes. The bile acids crossing and partitioning in the lipidic domain exert their activity in this microenvironment modifying the cholesterol content and therefore increasing the permeability to other substances.

A bile acid designed to be an enhancer, moreover, must be:

1) relatively lipophilic, with a partition coefficient octanol/water log P≧1;
2) relatively detergent, with a critical micell concentration ≦7±2 mM;
3) stable to intestinal bacterial flora and particularly not 7-dehydroxylated and oxidized to potentially toxic or inactive compounds.

Now it has been found that bile acids derivatives in which the side chain has one carbon atom more (NOR) or one less (HOMO) proved remarkable properties as absorption enhancers for medicaments by the enteral route and other not-parenteral routes (intranasal, buccal, sublingual).

Particularly, the best results were obtained with derivatives of the dehydroxylated bile acids above reported with two OH at the 3α7α, 3α7β, 3α6α, 3α12α and 3α12β positions. The choice of one of the above reported epimers will depend on the substance to carry. Compared with the natural derivatives, the nor- and homo-derivatives show the advantage that they are not metabolized by the intestinal bacterial flora and have a very high stability in anaerobic and aerobic fecal culture.

The change in the side chain can prevent a 7 dehydroxylation of the 3α7α and 3α7β derivatives with an enormous advantage compared with the natural components which are quickly metabolized.

The glycine- or taurine-amidated compounds also show a high stability to bacterial flora compared with physiological bile acids (BA) which are quickly deconjugated.

The derivatives of the invention are useful as absorption enhancers for medicaments administered by the enteral route or by other routes (intranasal, buccal, sublingual).

One of the most preferred administration routes is the rectal one, since these compounds are absorbed by the rectal mucosa and, once in circulation, the are immediately transformed into glucuronide derivatives at the hepatic level and excreted through the feces (even though they are not metabolized by the bacteria in the last intestinal tract, as already mentioned).

The general toxicity thereof is negligible even at doses 100 times higher than the envisaged ones.

The compounds of the invention can be obtained semi-synthetically according to known methods.

The medicaments which can be advantageously combined with iodeoxycholic acid belong in various chemical and/or therapeutical classes, such as peptides, not steroidal antiinflammatories, steroids, diuretics, cardiovasculars, hormones, local anaesthetics, antihistaminics, rhinologic and anticolinergic agents.

NORAB and HOMOAB, compared with the up to now known enhancers, particularly with other bile acids previously used (cholic and taurocholic acids) show the following advantages:
higher effectiveness;
lower toxicity;
metabolic stability towards the bacterial flora responsible for undesired biotransformations, such as the conversion of taurocholic acid into deoxycholic acid;
optimum lipohilia for the increase in cell membrane permeability, thanks to the capability of forming reverse micells inside which a part of membrane cholesterol dissolves, thereby the membrane becoming more permeable;
low detergency, which therefore causes no damages nor inflammations.

Examples of rectal formulations according to the invention comprise suppositories, microclysmas, soft gelatin rectal capsules.

For the intranasal administration, sterile solutions or powders are suitable, whereas oral or buccal forms comprise capsules, tablets, bioadhesive tablets and the like.

The preparation techniques and the excipients used for the preparation of said pharmaceutical forms are the conventional ones known, for example, from Remington's Pharmaceutical Sciences, Mack Pub., Co. N.Y., USA, XVII Ed.

For the oral use, the presence of NORAB and/or HOMOAB enhances the absorption of some active principles such as NSADs, diuretics and the like.

For the oral administration, the action of the derivatives of the invention takes place mainly at the duodenal and intestinal levels, therefore, in order to optimize the absorption, gastroresistant forms or controlled-release forms are preferably used, allowing the tablet to disintegrate at well-controlled pH values which are characteristic of a particular portion of the intestinal tract.

According to the invention, NORABs and HOMOABs are used in amounts from 0.1 to 100 mg per unitary dose.

Preferably, for the oral, buccal and rectal forms, they are present in amounts from 10 to 40 mg per unitary dose, whereas for intranasal forms they range from 0.5 to 10 mg per unitary dose.

The following examples further illustrate the invention. In said examples, Enhancer HOMOAB1, Enhancer NORAB1, Enhancer HOMOAB2, Enhancer NORAB2, Enhancer HOMOAB3, Enhancer NORAB4, Enhancer HOMOAB5 and Enhancer NORAB5 means, respectively, the following acids: homochenodeoxycholic, norchenodeoxycholic, homoursodeoxycholic, norursodeoxycholic, homodeoxycholic, 24-nor-[3α,12β-dihydroxy-5β-cholan-23-oic], 24-homo-[3α-6β-dihydroxy-5β-cholan-23-oic] and 24-nor[3α-6β-dihydroxy-5β-cholan-23-oic].

EXAMPLE 1

Diclofenac suppositories

One suppository contains:

| | |
|---|---|
| Sodium diclofenac | 100 mg |
| Enhancer HOMOAB1 | 20 mg |
| Whitepsol H 15 q.s. to | 2,5 g |

EXAMPLE 2

Calcitonin rectal capsules

One soft gelatin capsule for rectal use contains:

| | |
|---|---|
| Synthetic salmon calcitonin | 100 I.U. |
| Enhancer NORAB1 | 20 mg |
| Vaseline oil q.s. to | 700 mg |

EXAMPLE 3

Dipyrone coated tablets

One coated tablet contains:

| | |
|---|---|
| Dipyrone | 250 mg |
| Starch | 125 mg |
| Enhancer HOMOAB2 | 100 mg |
| Microcrystalline cellulose | 150 mg |
| Talc | 30 mg |
| Magnesium stearate | 20 mg |
| PVP K30 | 30 mg |
| Methacrylic acid polymer | 10 mg |
| Diethyl phthalate | 0,5 mg |

EXAMPLE 4

Furosemide tablets

One tablet contains:

| | |
|---|---|
| Furosemide | 20 mg |
| Enhancer NORAB2 | 20 mg |
| Starch | 50 mg |
| Lactose | 50 mg |
| PVP K30 | 3 mg |
| Talc | 1 mg |
| Magnesium stearate | 1 mg |
| Croscaramellose | 5 mg |

EXAMPLE 5

| Metronidazole tablets | |
|---|---|
| One tablet contains: | |
| Metronidazole | 250 mg |
| Microcrystalline cellulose | 200 mg |
| Starch | 130 mg |
| Enhancer HOMOAB3 | 100 mg |
| Talc | 10 mg |
| Sodium amidoglycolate | 100 mg |

EXAMPLE 6

| LHRH for buccal use: | |
|---|---|
| One administration unit contains: | |
| LHRH | 50 mcg |
| Starch | 80 mg |
| Carboxyvinyl polymer | 100 mg |
| Enhancer NORAB4 | 20 mg |

EXAMPLE 7

| LHRH for intranasal administration: | |
|---|---|
| One administration unit contains: | |
| LHRH | 50 mcg |
| Enhancer HOMOAB5 | 5 mg |
| Mannite q.s. to | 20 mg |

EXAMPLE 8

| GRH for intranasal administration: | |
|---|---|
| One administration unit contains: | |
| GRH | 50 mcg |
| Enhancer NORAB5 | 2,5 mg |
| Mannite q.s. to | 20 mg |

We claim:

1. A method of enhancing the absorption of a medicament by an animal, comprising adminstering to an animal the medicament in conjunction with a component selected from the group consisting of nor- and homo-bile acids derivatives of the following respective formulae:

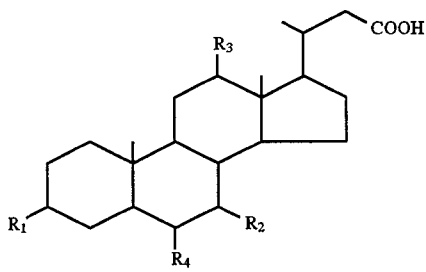

(I)

wherein:

| | $R_1$ | $R_2$ | $R_3$ | $R_4$ |
|---|---|---|---|---|
| a) | α-OH | α-OH | H | H |
| b) | α-OH | β-OH | H | H |
| c) | α-OH | H | α-OH | H |
| d) | α-OH | H | β-OH | H |
| e) | α-OH | H | H | β-OH |

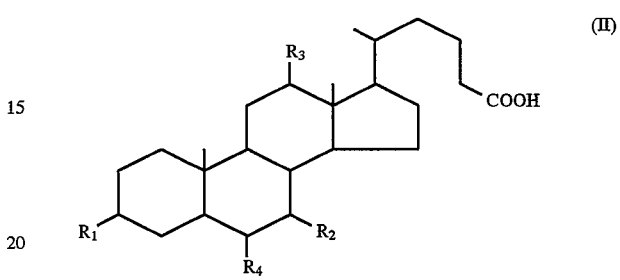

(II)

wherein:

| | $R_1$ | $R_2$ | $R_3$ | $R_4$ |
|---|---|---|---|---|
| a) | α-OH | α-OH | H | H |
| b) | α-OH | β-OH | H | H |
| c) | α-OH | H | α-OH | H |
| d) | α-OH | H | β-OH | H |
| e) | α-OH | H | H | β-OH | and conjugates of the above derivatives at positions $C_{23}$ or $C_{25}$ with taurine, glycine or alanine.

2. The method of claim 1, wherein the absorption takes place in the gastrointestinal tract.

3. The method of claim 1, wherein the absorption takes place at the buccal mucosa.

4. The method of claim 1, wherein the absorption takes place in the duodenal tract.

5. The method of claim 1, wherein the absorption takes place in the intestinal tract.

6. The method of claim 1, wherein the absorption takes place in the rectal tract.

7. The method of claim 1, wherein the absorption takes place in the nasal cavity.

8. The method of claim 1, wherein the medicaments are selected from the group consisting of peptides, not steroidal antiinflammatories, steroids, diuretics, cardiovasculars, hormones, local anaesthetics, antihistaminics, and anticolinergics.

9. The method of claim 1, wherein the administration is by a pharmaceutical form selected from the group consisting of a suppository, solution, powder, capsule, and tablet.

10. The method of claim 1, wherein said nor- and homo-bile acid derivative or conjugate is administered in amounts of between 0.1 and 100 mg per unitary dose.

11. The method of claim 10, wherein said amount is from 10 to 40 mg.

12. The method of claim 10, wherein said amount is 0.5 to 10 mg.

13. The method of claim 1, wherein said medicament and said nor and homo-bile acid derivative or conjugate are separately administered.

14. The method of claim 1, wherein said medicament and said nor- and homo-bile acid derivative or conjugate are co-administered.

15. The method of claim 14, wherein the said medicament and said nor- and homo-bile acid derivative or conjugate are both present in and co-administered by a pharmaceutical form selected from the group consisting of a suppository, solution, powder, capsule, tablet and bioadhesive.

* * * * *